United States Patent
Morschhäuser et al.

(10) Patent No.: US 10,150,749 B2
(45) Date of Patent: Dec. 11, 2018

(54) METHOD FOR OBTAINING VITAMIN E, STEROLS AND/OR TERPENES FROM OILY OR FATTY MIXTURES OF BIOLOGICAL ORIGIN

(71) Applicant: WeylChem Wiesbaden GmbH, Wiesbaden (DE)

(72) Inventors: Roman Morschhäuser, Mainz (DE); Said Kchirid, Heigenbrücken (DE); Hans Jürgen Scholz, Alzenau (DE)

(73) Assignee: WeylChem Wiesbaden GmbH, Wiesbaden (DE)

( * ) Notice: Subject to any disclaimer, the term of this patent is extended or adjusted under 35 U.S.C. 154(b) by 184 days.

(21) Appl. No.: 15/320,384

(22) PCT Filed: May 29, 2015

(86) PCT No.: PCT/EP2015/001094
§ 371 (c)(1),
(2) Date: Dec. 20, 2016

(87) PCT Pub. No.: WO2015/197155
PCT Pub. Date: Dec. 30, 2015

(65) Prior Publication Data
US 2018/0208571 A1      Jul. 26, 2018

(30) Foreign Application Priority Data
Jun. 24, 2014    (DE) .................. 10 2014 009 237

(51) Int. Cl.
*C07D 311/72*       (2006.01)
*C07B 63/02*        (2006.01)

(52) U.S. Cl.
CPC ............ *C07D 311/72* (2013.01); *C07B 63/02* (2013.01); *Y02P 20/544* (2015.11)

(58) Field of Classification Search
CPC ............................. C07D 311/72; C07B 63/02
USPC ........................................................ 554/174
See application file for complete search history.

(56) References Cited

U.S. PATENT DOCUMENTS

| | | | |
|---|---|---|---|
| 2,704,764 | A | 3/1955 | Mattikow et al. |
| 3,122,565 | A | 2/1964 | Kijima et al. |
| 3,153,055 | A | 10/1964 | Brown et al. |
| 5,190,618 | A | 3/1993 | Top et al. |
| 5,487,817 | A | 1/1996 | Fizet |
| 5,627,289 | A | 5/1997 | Jeromin et al. |
| 6,815,551 | B2 | 11/2004 | Albiez et al. |
| 9,000,197 | B2 | 4/2015 | Krull et al. |
| 2012/0103790 | A1 | 5/2012 | Krull et al. |

FOREIGN PATENT DOCUMENTS

| | | |
|---|---|---|
| DE | 3126110 A1 | 1/1983 |
| DE | 4228476 A1 | 3/1994 |
| EP | 0610742 A1 | 8/1994 |
| EP | 1122250 A1 | 8/2001 |
| EP | 2448905 A2 | 5/2012 |
| WO | 2002012222 A1 | 2/2002 |
| WO | 2003080778 A2 | 10/2003 |
| WO | WO-03080778 A2 * | 10/2003 ............... B01D 3/14 |

(Continued)

OTHER PUBLICATIONS

Paolo Bondioli et al., "Squalene Recovery from Olive Oil Deodorizer Distillates"; Journal of the American Oil Chemists' Society, Aug. 1993, pp. 763-766; vol. 70, No. 8, Springer-Verlag.
Syed Tufail Hussain Sherazi et al., "Vegetable Oil Deodorizer Distillate: A Rich Source of the Natural Bioactive Components"; Journal of Oleo Science, Nov. 9, 2016, pp. 1-10, vol. 65, No. 12, Japan Oil Chemists' Society, Tokyo.
Third Party Observation for Application No. EP20150734566, dated Sep. 14, 2017.

*Primary Examiner* — Deborah D Carr
(74) *Attorney, Agent, or Firm* — Michael Ferrell

(57) ABSTRACT

Disclosed is a continuous process for concentrating or separating of vitamin E, sterols and/or terpenes from oily or fatty mixtures of biological origin comprising the measures:

a) providing a reaction mixture containing oily or fatty mixture of biological origin, at least a monohydric alcohol and at least an acidic catalyst, b) continuously conducting the reaction mixture through a reactor which has a heating zone in which the reaction mixture is heated to a temperature between 100° C. and 190° C., measured with a temperature sensor immediately after leaving the heating zone, and in which the reaction mixture is under such pressure, that the reaction mixture is in liquid, critical or supercritical state, c) adjusting the flow velocity of the reaction mixture that its dwell time in the heating zone is up to 10 minutes, d) separating the product mixture from step c) into a polar phase containing the glycerol formed during the transesterification, the non-reacted monohydric alcohol, the acidic catalyst, and the reaction water that has been formed during the esterification of the oily or fatty mixture, and into a non-polar phase containing the fatty acid esters, that have been formed during the esterification and transesterification, and therein dissolved and/or dispersed secondary ingredients, and e) separating the fatty acid esters formed by esterification and by transesterification from the non-polar phase from step d) under formation of a residue containing vitamin E, sterols and/or terpenes.

The treatment of the oily or fatty mixtures proceeds under mild conditions so that the ingredients vitamin E, sterols and/or terpenes contained therein are damaged to an negligible amount and remain in the residue in high concentration.

20 Claims, No Drawings

(56) References Cited

FOREIGN PATENT DOCUMENTS

| WO | 2011000463 A2 | 1/2011 |
|---|---|---|
| WO | 2011035853 A1 | 3/2011 |

* cited by examiner

METHOD FOR OBTAINING VITAMIN E, STEROLS AND/OR TERPENES FROM OILY OR FATTY MIXTURES OF BIOLOGICAL ORIGIN

CLAIM FOR PRIORITY

This application is a national phase application of PCT/EP2015/001094 FILED May 29, 2015, which was based on application DE 10 2014 009 237.2 FILED Jun. 24, 2014. The priorities of PCT/EP2015/001094 and DE 10 2014 009 237.2 are hereby claimed and their disclosures incorporated herein by reference.

TECHNICAL FIELD

The present invention relates to a method for obtaining vitamin E, sterols and/or terpenes from oily or fatty mixtures of biological origin, and to the use of electromagnetic radiation, preferably in the micro wave band, or of heat exchangers for the production of such substances.

BACKGROUND

The oily or fatty mixtures originate from fats and fatty oils of biological origin, i.e. from plant, animal or microbial origin, and are known to be mixtures of different ingredients.

Fats and fatty oils are mixtures where esters of glycerol with three mostly different, predominantly even-numbered and unbranched aliphatic mono carboxylic acids, the fatty acids, make up the majority of the mixture. Compounds of this type are also called triglycerides. In addition to the glycerides fats and fatty oils contain accompanying substances that are usually grouped together in the technical literature as "unsaponifiable fractions". These are ingredients of the so-called plant secondary metabolism, including vitamin E, sterols and/or terpenes.

Depending on whether the compound mixture is solid or liquid at room temperature, it is called fat or fatty oil. Most fats are the eponymous compositions from different fatty acid triglycerides, which are obtained from animals. The term fatty oil distinguishes the (thin) fluid mixtures of materials of biological origin from other groups of oils, for example, from the liquid hydrocarbons.

Fats and fatty oils from biological origin are obtained either from animal products, from plants or from microorganisms, such as bacteria or yeasts but also from algae or fungi. Animal fats can be melted directly from adipose tissue and apply as lard, blubber or tallow, or can be obtained from milk. The vegetable oils and fats used for food can be obtained from oil plants or oilseed by pressure or by extraction with steam, supercritical $CO_2$ or solvents. Refining removes unwanted ingredients and refined fats or fatty oils are thereby graded up for use.

Newly substantial amounts of vegetable oils, particularly rapeseed oil or palm oil, are chemically reacted to biodiesel. For this purpose the oils are submitted to a transesterification with methanol in the presence of mostly alkaline catalysts, whereupon fatty acid methyl esters (FAME) and glycerol are formed. The former can be used directly as biodiesel or are mixed with conventional fuel. Furthermore, soaps, the alkali salts of fatty acids, can be produced by alkaline hydrolysis of fats or fatty oils. Thereby also glycerol accumulates as a secondary component.

The use of fats and fatty oils as food and in the making of food as well as in the preservation of food is widespread.

Native fats and fatty oils directly after pressing are often not suitable for direct consumption and must be released in a pre-cleaning from bitters, free fatty acids, dyes and other undesired accompanying substances affecting taste and aesthetics. This is achieved by using two different techniques, referred to as chemical or physical refining. Today, in the vast extent the physical purification to edible oils is preferred due to economic considerations. Under high pressure, hypertensive water vapor at temperatures above 200° C. is guided through the oil to be cleaned. In doing so the water vapor entrains all volatile portions that after condensation and pressure relaxation can be attained as so-called deodorization distillates. In the literature these "waste components" are designated as oleo-waste, as DDO ("Deodorization Distillates Oils"), as condensates ("Oil Physical Refining Condensate" or "OPRC") or in the predominate case in the English-speaking world as FAD ("Fatty Acid Distillates").

"Oily and fatty mixtures" are understood in terms of the invention as fats and fatty oils of biological origin but also as the "waste components" denominated in the preceding, in particular DDO and OPRC, but also waste components of fats and oils, which are accumulated in the food industry and gastronomy.

The "unsaponifiable fractions" contained in the oily and fatty mixtures are ingredients of the so-called secondary metabolism, especially of plant secondary metabolism. These chemically and functionally very different compounds are called "secondary ingredients" in the remainder of this description. Chemically considered these secondary ingredients are complicated olefinic, aliphatic or aromatic alcohol components or terpenes, which display different physiological effects in plants but also in animals.

A very valuable portion of this substance group not only for human physiology are the vitamins of the E-series. The basic structure of all forms of vitamin E forms a chromane ring hydroxylated at position 6, whose methylation divides these into a $\alpha$-, $\beta$-, $\gamma$- or $\delta$-form. Two main families are distinguished by side chains of different saturation, namely the saturated tocopherols and the triple unsaturated tocotrienols. Also additional species (tocomonoenols), which can be denominated rather than exotic, can be included in the vitamin E.

Vitamin E is a component of all animal cell membranes, is however made only by photosynthetic active organisms such as plants and cyanobacteria, and must be ingested therefore by animals and humans through food. Out of the eight most important representatives of the naturally occurring vitamin E series $\alpha$-tocopherol is the substance with the strongest physiological effect and therefore also with the greatest technical and economic importance. The individual members of the tocopherol family differ in the degree of methylation of their benzene nucleus or in the case of tocotrienols in the degree of saturation of the side group.

Especially high concentrations of vitamin E are contained in vegetable oils like wheat germ oil (up to 2435 mg/kg total tocopherol with 70% $\alpha$-tocopherol), sunflower oil (454-810 mg/kg total tocopherol with 86-99% $\alpha$-tocopherol), red palm oil (800 mg/kg total vitamin E, of which 152 $\alpha$-tocopherol and 600 mg/kg tocotrienols) and olive oil (46-224 mg/kg total tocopherol with 89-100% $\alpha$-tocopherol). The dose- and matrix-dependent absorption rate is on average at 30%.

Vitamin E is also synthetically produced as a racemic mixture (among others by BASF, E. Merck (India) and DSM Nutritional Products). Synthetic tocopherol is relatively unstable and is provided thereby mostly with an acetyl group (see also dl-$\alpha$ tocopheryl acetate). This does not have antioxidant properties. But it can be converted in the body to the extent of up to 50% into natural vitamin E.

Just as valuable components of the unsaponifiable fraction of oily or fatty mixtures of fats and fatty oils of biological origin are sterols, which are important biochemical natural products for the pharmaceutical, cosmetics and food industry. The sterols—also called sterines—are an important subgroup of steroids. Basic framework is the sterine, a sterane with a 3β-hydroxyl group. Depending from their occurrence sterins can be divided in zoo sterols (from animals), phytosterols (from plants) and mycosterines (from fungi). Important zoo sterols are cholesterol and coprosterine that is formed by bacteria from cholesterol in the intestine. Stigmasterine (stigmasterols) occurring in soybeans, camposterine (camposterol) and also sitosterine (sitosterol) are counted among the phytosterols. Several phytosterols occur also in wheat seedlings. Counted among the group of mycosterines is e.g. ergosterine (ergosterol) isolable from yeasts, which is closely related to the vitamines of the D series.

Terpenes are another group of secondary ingredients that occur in fats and fatty oils of biological origin and that belong to the unsaponifiable fraction. This substance class, that is separable through the process of the invention, is a very large and highly heterogeneous group of chemical compounds which occur naturally in many organisms. They formally derive from isoprene and are characterized by a great variety of carbon frameworks with functional groups. Most of the terpenes are of vegetal origin and seldom of animal origin. Predominantly hydrocarbon-, alcohol-, glycoside-, ether-, aldehyde-, ketone-, carboxylic acid- and ester-terpenes occur in nature, but also representatives of other groups of substances can be found among the terpenes.

Terpenes are often of biological and pharmacological interest. They can be used e.g. as environmentally friendly insecticides in that they lure insects into traps as pheromones. In addition, many operate anti-microbial. Many terpenes are used in perfumes and cosmetic products as odors or flavors.

In the context of the present description among terpenes hydrocarbon compounds and also oxygenous isoprene derivatives are understood, whereupon the latter are sometimes also designated as terpenoids.

Terpenes are counted among the lipids in the systematics of organic chemistry. The affiliation to the terpenes is based in a common biosynthesis and in the $C_5$ rule, but not in common properties. Common building block of all terpenes is isoprene.

Generally one distinguishes between acyclic, mono-, bi-, tri-, tetra- and pentacyclic terpenes, thus molecules without, with one, two, three, four or five rings. Furthermore, terpenes can be differentiated by the carbon framework on which they are built. Also, they are classified through their secondary affiliation of element groups.

Terpenes can be divided into isoprene units, which have the same number of carbon atoms. Terpenes with 5 carbon atoms are called hemiterpenes ($C_5$), with 10 mono-terpenes ($C_{10}$), with 15 sesquiterpenes ($C_{15}$), with 20 diterpenes ($C_{20}$), with 25 sester terpenes ($C_{25}$), with 30 triterpenes ($C_{30}$), and with 40 tetraterpenes ($C_{40}$). Terpenes with more than 8 isoprene units, thus with more than 40 carbon atoms are called poly terpenes (greater than $C_{40}$). Here, the isoprene unit is counted as half a terpene.

Squalene is a particularly preferred terpene. It is an unsaturated organic compound with the molecular formula $C_{30}H_{50}$ from the group of triterpenes produced by all higher organisms. The compound is an integral part of skin lipids and is also found in the human blood serum. Squalene is present in high concentration levels in different foods, such as in goat's milk and in many vegetable oils, such as olive oil, wheat germ oil or rice bran oil. Fish oils are the main resources. Squalene is used industrially and is hydrogenated to squalane, which is used as a basis for ointments as well as a lubricant and a transformer oil.

Preferred sources of these secondary ingredients are particularly oils and fats of vegetable origin, in particular acai oil, algae oil, apricot kernel oil, argan oil, avocado oil, babacu oil, cotton seed oil, ben oil, borage oil, nettle seed oil, cashew shell oil, cupuaçu butter, thistle oil, peanut oil, safflower oil, hemp oil, rosehip seed oil, hazelnut oil, jathropha oil, jojoba oil, coffee bean oil, cocoa butter, camellia oil, coconut oil, cumin oil, pumpkin seed oil, linseed oil, cameline oil, macadamia oil, corn oil, almond oil, mango butter, poppy-seed oil, evening primrose oil, olive oil, palm oil, palm kernel oil, papaya seed oil, pecan oil, perilla oil, pistachio oil, rapeseed oil, rice oil, castor oil, sea buckthorn seed oil, sea buckthorn oil, black cumin oil, mustard oil, sesame oil, shea butter, soybean oil, sunflower oil, grape seed oil, tung oil, walnut oil, watermelon seed oil or wheat germ oil.

Depending on the origin, vegetable fatty oils or fats contain a proportion of non-saponifiable secondary ingredients of about 0.5 to 5% by weight, animal fat oils or fats a lesser proportion, to which vitamin E, terpenes and sterols are counted.

Deodorization distillates (DDO or OPRC) contain higher levels of secondary plant ingredients.

To separate these non-saponifiable components of fatty acids and glycerides (fat components) different methods are available, such as disclosed in "The Encyclopedia of Vitamin E, ISBN 978-1-84593-075-2, pp. 140-141. A common method for the separation of the fat components from tocopherol is the esterification of free fatty acids followed by a transesterification step with subsequent distillative separation of the esters.

State of the art is that fatty acids and glycerides are transferred into fatty acid methyl esters by esterification of the fatty acids and by transesterification of the glycerides with short-chain alcohols, preferred with methanol, which can be isolated by distillation. An esterification of fatty acids and a transesterification of glycerides does not succeed in conventional procedures in a single reaction step, but requires the esterification of the fatty acid in a first step and the transesterification of the glycerides in a subsequent step.

The transesterification of the glycerides is normally performed in alkaline medium, because the reaction speed in the acidic environment is much too low and requires significantly more drastic conditions. The presence of alkaline reagents leads but to the neutralization of free fatty acids and disrupts the transesterification reaction of the glycerides (partial saponification). For this reason in practice an acid esterification of the free fatty acid content is operated beforehand, as described in the following patent.

U.S. Pat. No. 5,190,618 teaches to separate the non-saponifiable components from the glycerides and the free fatty acids in that in a first step the free fatty acids are esterified with a short-chain alcohol, for example with methanol, in the presence of an acid catalyst, for example p-toluene sulfonic acid, at 65 to 110° C., and in a second reaction step the glyceride portions are transesterified with a short-chain alcohol, e.g. methanol, in the presence of an alkaline catalyst, for example sodium methoxide, at 30 to 70° C. and the obtained fatty acid alkyl esters are distilled off. The tocopherol and tocotrienol enriched in the residue is obtained in high concentrations by crystallization, ion exchange processes and distillation. This procedure is very laborious and also has the disadvantage that tocopherol and the sterols also present under the chosen reaction conditions in the acid medium are very easily esterified with free fatty acids. In the therefore necessary alkaline reaction section these esters are then split subsequently into the free components again, however there will be a very noticeable degradation of the tocopherol due to its oxidative instability in the basic environment.

U.S. Pat. No. 5,487,817 discloses a method for the isolation of tocopherol and sterols from a mixture consisting essentially of tocopherol, sterols, fatty acids and glycerides. In the process the sterols are esterified in the course from 1 to 12 hours at 150 to 250° C. without acidic or alkaline catalysis and remnants of fatty acid, tocopherol and sterol fatty acid esters are separated by several distillation steps at 150 to 220° C. under vacuum.

The sterol fatty acid esters contained in the residue are transesterified by acid catalysis and are isolated from the glyceride. It is known (Acta Agric Scan 35: 136-138 (1985)), that temperatures above 120° C. result in significant degradation of tocopherol, whereby the yields of tocopherol are reduced. Also, a smaller amount of tocopherol is esterified in this procedure in the presence of fatty acids, and this causes a further loss of vitamin E. Likewise, sterols are temperature- and light-sensitive and are destroyed in part under the conditions.

EP-A-2,448,905 describes a continuous process for producing aliphatic carboxylic acid esters by reaction of aliphatic carboxylic acids with alcohol in the presence of an esterification catalyst under exposure to microwave radiation.

WO-A-2011/035853 describes a continuous process for producing fatty acid methyl esters through transesterification of fatty acid esters of multi-valent alcohols, in particular glycerides, with methanol in the presence of alkaline or acidic catalysts under exposure to microwave radiation. The procedure allows the production of high-purity fatty acid methyl esters from native fats and oils in large scale processes, or from the waste products from their refining, even in the presence of free acids. Procedures for the isolation of other ingredients from the native oils or fats or from the waste products of native oils or fats is not the subject of the invention.

The methods for the separation of non-saponifiable ingredients from DDO's or OPRC's referred to in the prior art are energy intensive and are unsatisfactory regarding the yield of the physiologically particularly valuable secondary ingredients, such as vitamin E, especially α-tocopherol, tocotrienols, sterols and terpenes.

SUMMARY OF INVENTION

Surprisingly it was found that the secondary ingredients vitamin E, sterols and terpenes from oily or fatty mixtures of biological origin can be separated in high yield, preferably in yields of greater than 90%, based on the initial concentration of these secondary ingredients, from the fat components consisting essentially of fatty acids and glycerides. This is achieved by a continuous process in which in a single-stage acid catalyzed reaction an oily or fatty mixture and a monohydric alcohol containing reaction mixture is treated in a continuous reactor, which has a heating zone, under the influence of high temperatures and high pressure, whereby the duration of the energy input and the residence time of the reaction mixture in the heating zone is comparatively short.

The product separated from the components fatty acid, fatty acid esters and glycerol contains surprisingly high yields of vitamin E, sterols and/or terpenes.

The subject-matter of the invention is a continuous process for concentrating or separating of vitamin E, sterols and/or terpenes, especially tocopherol, tocotrienols and/or sterols, from oily or fatty mixtures of biological origin with the measures:

a) providing a reaction mixture containing an oily or fatty mixture of biological origin, at least a monohydric alcohol, preferably methanol or ethanol, and at least an acidic catalyst, b) continuously conducting the reaction mixture through a reactor, in particular through a tubular reactor, which has a heating zone in which the reaction mixture is heated to a temperature between 100° C. and 190° C., preferably between 160° C. and 180° C. and particularly preferably between 165° C. and 175° C., measured with a temperature sensor immediately after leaving the heating zone, and in which the reaction mixture is under such pressure, that the reaction mixture is in liquid, critical or supercritical state, preferably under a pressure between 2 and 250 bar, particularly preferred between 6 and 200 bar, particularly preferred between 7 and 50 bar, and most preferably between 15 and 25 bar, c) adjusting the flow velocity of the reaction mixture that its dwell time in the heating zone is up to 10 minutes, preferably up to 8 minutes, particularly preferred up to 5 minutes, especially preferred up to 1 minute and extremely preferred up to 40 seconds, d) separating the product mixture from step c) into a polar phase containing the glycerol formed during the transesterification, the non-reacted monohydric alcohol, the acidic catalyst, and the reaction water that has been formed during the esterification of the oily or fatty mixture, and into a non-polar phase containing the fatty acid esters, that have been formed during the esterification and transesterification, and therein dissolved and/or dispersed secondary ingredients, and e) separating the fatty acid esters formed by esterification and by transesterification from the non-polar phase from step d) under formation of a residue containing vitamin E, sterols and/or terpenes.

With the process of the invention secondary ingredients selected from vitamin E, sterols and/or terpenes are obtained in high concentrations without significant degradations, conversions, especially without esterification or rearrangement of chemical structures of the active ingredients. With the process of the invention in process step c) fatty acid esters and free fatty acids are ersterified and transesterified in the same reaction mixture.

The residue obtained after step e) of the process of the invention contains for example, at least 70%, preferably at least 80% and especially preferred at least 95% of the starting quantity of vitamin E, sterols and/or terpenes, particularly of α-tocopherol and/or β-sitosterol, stigmasterol, and campestol, which cannot be isolated by known methods, for example by extraction, such as by extraction with supercritical $CO_2$, or by chromatography.

In the process of the invention an esterification of tocopherols and sterols with free fatty acids, contrary to expectations, has not or has almost not taken place to a detectable level. Neither tocopherol fatty acid ester nor sterol fatty acid esters have been detected using gas chromatography/mass spectroscopy. In the residue obtained in process step e) of the process of the invention free tocopherols and free sterols in high purity were detected by means of GC/MS, preferably in concentrations of >95%, based on the weight of the starting amount of tocopherols and sterols.

With the process of the invention the heat-sensitive secondary plant ingredients vitamin E, sterols and/or terpenes, particularly tocopherols and sterols, can be obtained in high concentrations without significant transformation or degradation of these secondary plant ingredients, for example in amounts of >5% by weight, based on the weight of these secondary plant ingredients in the oily or fatty mixture of biological origin.

The process of the invention is therefore distinguished in that only small quantities of vitamin E, sterols and terpenes are lost by degradation.

The process of the invention is especially distinguished in that vitamin E and sterols can be gained in the free, not esterified form on the basis of natural raw materials. Further details are provided below.

DETAILED DESCRIPTION

The oily or fatty mixtures from fatty oils or fats of biological origin can be used in the process of the invention as such or as distillates individually or in the form of mixtures or combined with organic solvents or thinners or in the form of dispersions. Examples of solvents and thinners are aliphatic or aromatic hydrocarbons or aprotic organic solvents. The preferred distillates of fats and fatty oils can be used alone or in a mix of two or more of such distillates in the process of the invention.

Preferably used are oily or fatty mixtures of oils or fats of vegetable origin, particularly vegetable oils selected from acai oil, algae oil, apricot kernel oil, argan oil, avocado oil, babacu oil, cotton seed oil, ben oil, borage oil, nettle seed oil, cashew shell oil, cupuaçu butter, thistle oil, peanut oil, safflower oil, hemp oil, rosehip seed oil, hazelnut oil, jathropha oil, jojoba oil, coffee bean oil, cocoa butter, camellia oil, coconut oil, cumin oil, pumpkin seed oil, linseed oil, cameline oil, macadamia oil, corn oil, almond oil, mango butter, poppy-seed oil, evening primrose oil, olive oil, palm oil, palm kernel oil, papaya seed oil, pecan oil, perilla oil, pistachio oil, rapeseed oil, rice oil, castor oil, sea buckthorn seed oil, sea buckthorn oil, black cumin oil, mustard oil, sesame oil, shea butter, soybean oil, sunflower oil, grape seed oil, tung oil, walnut oil, watermelon seed oil or wheat germ oil, and especially of wheat germ oil, corn oil, rapeseed oil, soybean oil, sunflower oil, olive oil and/or palm kernel oil.

Particularly preferred are oily or fatty mixtures used, which are obtained by physical refining of vegetable oils and which are called deodorization distillates ("Deodorization Distillates Oils" or "DDO") and condensates ("Oil Physical Refining Condensate" or "OPRC"). These include besides fatty acids and glycerides a higher proportion of non-saponifiable ingredients, compared to the unrefined oil.

In the process of the invention the reaction mixture according to process step a) contains one or more monohydric alcohols for the esterification of fatty acids or for the transesterification of triglycerides and/or phospholipids.

This is usually a monohydric aliphatic alcohol or a mixture of such alcohols. These contain generally one to six carbon atoms. The monohydric aliphatic alcohols can be straight-chain or branched.

Examples of preferably used alcohols are methanol, ethanol, n-propanol, iso-propanol, n-butanol, iso-butanol, tert-butanol, preferably methanol and ethanol, especially preferred methanol.

The molar ratio of monohydric aliphatic alcohol, especially of methanol, to esterifyable or transesterifyable groups consisting of COOH groups and/or from ester groups is greater than 1.

In a preferred embodiment of the process of the invention the molar ratio of monohydric aliphatic alcohol, in particular of methanol, to esterifyable or transesterifyable groups in the reaction mixture is from 1 to 20, preferably from 1.5 to 10, in particular from 1.7 to 6, and especially favored from 2 to 5.

Esterification or transesterification catalysts used In the process of the invention are acid catalysts or mixtures thereof. These can be inorganic, metal-organic and/or organic acid compounds. As acid inorganic catalysts in terms of the present invention mineral acids can be used, such as hydrochloric acid, boric acid, nitric acid, sulfuric acid, phosphoric acid, phosphonic acid, or hypophosphorous acid; acid salts can also be used, such as aluminium sulfate hydrate, alum, acidic silica gel or acid aluminium hydroxide. Additional acidic inorganic catalysts are, for example, aluminium compounds of the general formula $Al(OR^3)_3$ and titanate of general formula $Ti(OR^3)_4$, where the residues $R^3$ can be equal or different and are selected independently of one another from $C_1$-$C_{10}$-alkyl residues, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, sec.-hexyl, n-heptyl, n-octyl, 2-ethylhexyl, n-nonyl or n-decyl, from $C_3$-$C_{12}$-cycloalkyl groups, for example, cyclopropyl, cyclobutyl, cyclopentyl, cyclohexyl, cycloheptyl, cyclooctyl, cyclononyl, cyclodecyl, cycloundecyl and cyclododecyl. Cyclopentyl, cyclohexyl and cycloheptyl are preferred. Preferably, the residues $R^3$ in $Al(OR^3)_3$ or $Ti(OR^3)_4$ are each equal and are selected from isopropyl, butyl and 2-ethylhexyl.

Preferred acid organometallic catalysts are selected from dialkyl tin oxides $(R^3)_2SnO$, where $R^3$ is defined as above. A particularly preferred representative for an acid organometallic catalyst is di-n-butyl tin oxide, which is commercially available as a so-called oxo-tin or as Fascat<(R)>-trademarks.

Preferred acidic organic catalysts are organic compounds containing acidic groups such as phosphate groups, phosphonic acid groups, sulfonic acid groups, sulphate groups or carboxylic acid groups. Especially preferred sulfonic acids contain at least a sulfonic acid group and at least a saturated or unsaturated, linear, branched and/or cyclic hydrocarbon residue with 1 to 40 C-atoms and preferably with 1 to 24 C-atoms.

Especially preferred are aromatic sulfonic acids and especially alkyl-aromatic mono sulfonic acids with one or more $C_1$-$C_{28}$-alkyl groups, and especially those with $C_1$-$C_{22}$ alkyl groups.

Preferred examples are methane sulfonic acid, butane sulfonic acid, benzene sulfonic acid, p-toluene sulfonic acid, xylene sulfonic acid, 2-mesitylene sulfonic acid, 4-ethylbenzene sulfonic acid, isopropylbenzene sulfonic acid, 4-butylbenzene sulfonic acid, 4-cctylbenzene sulfonic acid, dodecylbenzene sulfonic acid, didodecylbenzene sulfonic acid, naphthalene sulfonic acid.

Particularly preferred for the carrying out of the process of the invention are boric acid, phosphoric acid, polyphosphoric acid and polystyrene sulfonic acid.

Titanates of general formula $Ti(OR^3)_4$ and especially titaniumtetrabutylat and titaniumtetraisopropylat are particularly favored.

In another preferred embodiment solid acid catalysts are used in the process of the invention. Examples include zeolites, silica gel, acid layered silicates, such as montmorillonite and organic ion exchange resins.

The acidic catalysts are typically used in quantities of up to 10 wt. %, based on the total mass of the reaction mixture, preferably in quantities from 0.01 to 10 wt. %, and particularly preferred from 0.02 to 2 wt. %.

The reaction mixture containing the oily or fatty mixture, acidic catalyst and monohydric alcohol, is guided through a reactor. In the heating zone the reaction mixture experiences a strong heating through supply of heating output. This can be effected through heat transfer by physical contact with a hotter wall or by interaction between polar or ionic molecules with electromagnetic fields, for example with wavelengths in the centimeter range (microwaves).

According to the invention the reaction mixture is exposed to a sufficiently high heat output in the heating zone for a period of up to 10 minutes, preferably up to 8 minutes, especially preferred up to 5 minutes, more especially preferred up to 1 minute and most especially preferred up to 40 seconds, for example, from 0.01 to 40 seconds. The reaction mixture is experiencing thereby a strong temperature rise and has at the exit of the heating zone a temperature between 100° C. and 190° C., preferably between 160° C. and 180° C. and particularly preferably between 165° C. and 175° C., measured immediately after leaving the heating zone by using a temperature sensor.

The reaction mixture is under pressure in the reactor, so that the reaction mixture in the heating zone is in the liquid, critical or supercritical state, preferably under a pressure between 2 and 250 bar, particularly preferred between 6 and 200 bar, and especially preferred between 7 and 50 bar, and most especially preferred between 15 and 25 bar. The liquid, critical, or supercritical state of the reaction mixture is a prerequisite for an efficient heating of this mixture in the heating zone, especially in case that electromagnetic radiation is used, such as, for example, microwave radiation.

The dwell time in the heating zone is adjusted by selecting a suitable flow rate of the reaction mixture through this zone. Another preferred option in terms of the invention for the adjustment of the dwell time is a suitable choice of the apparatus size.

In one embodiment of the process of the invention a lingering line is connected to the heating zone of the reactor. After the dwell time in the heat zone the reaction mixture can remain in this lingering line for a retention period of up to 30 minutes, preferably from 0.5 to 600 seconds, particularly preferred from 5 to 300 seconds, and especially particularly preferred from 30 to 150 seconds.

The feeding of the required heating output in the heating zone can be effected by any device, which is able to enter temporarily high amounts of heating power into the reaction mixture. Examples of suitable devices are heat exchangers, in particular recuperators, or electromagnetic radiation in the micro wave band The known types can be used as recuperators. Examples of these are plate heat exchangers, capillary heat exchangers, micro reactors, spiral heat exchangers, tube bundle heat exchangers, U-tube heat exchangers, pipe heat exchangers, damper registers or countercurrent heat exchangers.

Preferably the reaction mixture is charged in the heating zone with high heating output by heating with electromagnetic radiation in the micro wave band or by means of a heat exchanger.

Especially preferred the heating zone is designed in the form of a pressure-resistant, microwave transparent pipe, which is located in a suitable sized cavity resonator, which is able to produce a resonant electromagnetic field, preferably in the micro wave band, of appropriate field strength, with whose help the reaction product is heated by dielectric heating mechanisms.

The used electromagnetic radiation preferably has a frequency in the range from 300 MHz to 30 GHz, in particular a frequency from 915 MHz, 2.45 GHz or 5.8 GHz.

Particularly preferably the cavity resonator is operated in mono mode.

By short-term exposure to high temperatures and pressures on the reaction mixture the esterification and transesterification reactions therein take place very fast and at the same time. In doing so most of the existing triglycerides, fatty acids and phospholipids are converted to fatty acid esters and free glycerol and reaction water is liberated.

In a preferred embodiment of the process of the invention in step d) the separation of the product mixture from step c) into a polar phase comprising the glycerol formed by transesterification, the not reacted monohydric alcohol, the acidic catalyst and the reaction water and into a non-polar phase containing the fatty acid esters and therein dissolved or dispersed the secondary ingredients by phase separation takes place, so that one of the phases substantially contains glycerol, monohydric alcohol, acidic catalyst and water and the second phase essentially contains fatty acid esters and therein dissolved or dispersed secondary ingredients.

In a subsequent step e) the phase containing the secondary ingredients is separated from the fatty acid esters, for example, by physical separating processes, preferably by membrane separation, by chromatographic processes, or in particular by distillation, whereby the resulting residue contains vitamin E, sterols and/or terpenes.

Extraction processes, in particular using supercritical $CO_2$ for concentrating or isolating these ingredients, are also suitable.

Particularly preferably used for the concentration or separation of vitamin E, the sterols and/or the terpenes from the fatty acid methyl esters are thin film evaporation, falling film evaporation and short path evaporation designated as "molecular distillation processes".

Moreover, remainders of undesired accompanying components, in particular remainders of non-reacted free fatty acids can be separated by washing with water, optionally also using auxiliary means, such as base or emulsion breakers.

The residue from process step e) comprising vitamin E, sterols and/or terpenes can be marketed as such or this is further processed to isolate individual desired ingredients thereof. The well-known separation processes can be used.

Examples of these are processes in which the separation takes place due to the different boiling points of the compounds to be separated. Examples of such processes are distillation, rectification or stripping.

Other examples of these are processes where the separation takes place due to the different melting points of to compounds to be separated. Examples of such processes are freezing out or fractional crystallization.

Other examples of separation processes are the separation of substances by sublimation including freeze-drying.

Still other examples for these are processes wherein the separation takes place due to the different solubility for the compounds to be separated. Examples of such processes are chromatographic process or extractive processes.

Preferably vitamin E, sterols and/or terpenes are concentrated and isolated by means of the process of the invention. For this purpose the residue from step e) comprising vitamin E, sterols and/or terpenes from step e) is processed to separate these resources from it.

In particular, the process of the invention can be used for the concentration or the isolation of sterols, and particularly of vitamin E.

The invention relates also to the use of heat exchangers, especially of recuperators, or applicators for micro waves to obtain vitamin E, sterols and/or terpenes from oily or fatty mixtures of biological origin.

The following examples are intended to illustrate the invention without restricting this to these examples.

All percentages are to be understood as weight percentages.

Example 1: Instruction for the Recovery of Tocopherol Concentrates from Deodorizer Distillates from the Refining of Soybean Oil or Sunflower Oil 3500 g of a DDO mixture were placed in a heated 10 liter mixing container and 1450 g methanol were added under stirring.

The DDO mixture had the following composition: 50 wt. % DDO from soybean oil, 50 wt. % DDO from sunflower oil.

After the mixture was prepared 50 g of sulfuric acid were added as a catalyst to the reaction mixture and the mixture was tempered at 50° C.

For carrying out the reaction the mixture was pumped with a speed of 6 liters/h and with a capacity of 0.8 kW through a continuously working micro wave equipment (p WaveFlow xx20/2450 MHz) of company PUschner GmbH. Thereby the product to be heated was heated at static working pressure of 25 bar to a temperature of 170° C., measured using a Pt100 temperature sensor immediately after having left the irradiation zone.

During the duration of the experiment the microwave power was set in a manner that the desired temperature of the products to be reacted was kept constant at the end of the irradiation zone. The micro wave powers referred to in the experiment descriptions therefore represent the time average of the radiated microwave power. The measurement of the temperature of the reaction mixture was made by means of a Pt100 temperature sensor directly after leaving the irradiation zone. Microwave energy not directly absorbed by the reaction mixture was reflected on the front face of the cavity resonator lying towards the coupling antenna; the microwave energy also not absorbed by the reaction mixture with the return and mirrored back in the direction of the magnetron was guided in a water load using a prism system (circulator). From the difference between the radiated energy and the power loss (determined by the heating of the water load) the microwave energy entered into the product to be reacted was calculated.

By means of a high pressure pump and a suitable pressure relief valve, the reaction mixture in the apparatus was under such working pressure, which was enough to keep all reactants and products or condensation products always in liquid form. The reaction mixtures were pumped with a constant flow rate through the device and the dwell time in the irradiation zone and downstream lingering line was adjusted by modification of the flow velocity.

The dwell time in the radiation zone was about 35 seconds.

The dwell time in the downstream lingering line was about 1 minute.

The reaction product was trapped in a phase separator and phases were separated.

The turnover determined by means of $^1$H-NMR (500 MHz in CDCl$_3$), relating to the free carboxylic acid and partial glycerides/glycerides in the educt mixture, was 93%.

For removal of methanol and carboxylic acid residues, the organic upper phase (4350 g) was stowed with 1450 g (⅓ of the amount) of 3% water/NaOH solution of 50° C. and stirred 1 hour. After another phase separation the aqueous sub phase was drained and the organic upper phase was largely released from water and methanol residues by applying a vacuum of 50 mbar. 3670 g of organic upper phase were obtained.

Afterwards a distillative separation of the volatile portions takes place in a thin film evaporator with an evaporator area of 150 cm$^2$ and a vacuum of 2-3 mbar at a forerun temperature of 230° C.

TABLE 1

Balance of distillation:

| extract (g) | sump (g) | distillate (g) | cold trap residue (g) | residue (%) | distillate (%) |
|---|---|---|---|---|---|
| 3670 | 510 | 3155 | 5 | 13.9 | 86.1 |

All non-volatile portions were trapped at the bottom of the thin film evaporator and were discharged as the desired concentrate. The determination of the vitamin E content was performed by means of HPLC using appropriate tocopherol calibration standards.

The concentration factor was determined as follows:

According to the distillation balance 86.1 wt. % of the original organic upper phase were separated by distillation and were identified as fatty acid methyl ester by using $^1$H-NMR spectroscopy.

There remained a residue consisting of 510 g sump and 5 g cooling trap residue, whereby the cooling trap residue did not contain any secondary ingredient.

The contents of tocopherol isomers, α-tocopherol, β-tocopherol, γ-tocopherol, and δ-tocopherol, both in the used soybean oil and the sunflower oil (DDO), as well as the contents of tocopherol isomer of the sump were determined using liquid chromatography and standard calibration and are summarized in table 2.

The content of tocopherol, consisting of the tocopherol isomers α-tocopherol, β-tocopherol, γ-tocopherol and δ-tocopherol in the used DDO from 50 wt.-% soybean oil, 50 wt.-% sunflower oil amounted to 1.91 wt.-%. Under the assumption that after the reaction and distillation 100% of the tocopherol from the tocopherol isomers α-tocopherol, β-tocopherol, γ-tocopherol and δ-tocopherol are in the sump, a weight proportion of 13.7% of tocopherol is to be expected in the sump.

Analytically determined was a tocopherol content of 13.3 wt.-%, consisting of the tocopherol isomers α-tocopherol, β-tocopherol, γ-tocopherol and δ-tocopherol, what corresponded to a 94.9% yield of tocopherol and to a concentration factor of 6.83.

TABLE 2 tocopherol contents in DDO consisting of soy-bean-and sunflower oil, as well as
tocopherol contents after effected reaction and distillation according to example 1

| DDO (orign) | tocopherol | | | | |
|---|---|---|---|---|---|
| | α | β | Υ | σ | sum |
| soy-bean | 0.15% | 0.05% | 0.82% | 0.50% | 1.52% |
| Sunflower | 2.10% | 0.13% | 0.05% | 0.02% | 2.30% |
| 50:50 mixture | 1.13% | 0.07% | 0.44% | 0.26% | 1.91% |
| Concentrate | | | | | |
| in theory | 8.10% | 0.50% | 3.20% | 1.9% | 13.7% |
| determined | 7.90% | 0.60% | 3.10% | 1.5% | 13.1% |

Example 2

The reaction conditions were analogous to those in example 1 with the difference that in this case a pure sunflower DDO had been used.

The contents of tocopherol prior to reaction (raw) and after reaction and reworking with the thin film evaporator (2. and 3.TFE) are shown in table 3.

The recovery rate was calculated using the distillation balance. In this example it is located at 97%.

TABLE 3 tocopherol contents in the originally non-reacted suflower oil DDO, as well as
tocopherol contents after reaction and distillation according of example 2

| DDO | tocopherol | | | | recovery |
|---|---|---|---|---|---|
| (origin) | A | β | Υ | σ | rate |
| sunflower | | | | | |
| starting material | 1.7 | 0.1 | <0.1 | <0.2 | n.b. |
| 2.TFE | 5.4 | 0.35 | <0.1 | <0.1 | n.b. |
| 3.TFE | 7.50 | 0.48 | <0.1 | <0.2 | 97% |

Example 3

The reaction conditions were similar to those of example 1 except that a soy DDO was used in this case.

The content of tocopherol prior to the reaction (raw) and after the reaction and work-up with the thin film evaporator (3a and 3b. TFE) are shown in table 4. The recovery rate was calculated using the distillation balance. In this example it is located at 95% or 98% (reproduction).

TABLE 4 tocopherol contents in the DDO, consisting of soybean oil, as well as
tocopherol contents after reaction and distillation as shown in example 3

| DDO | Tocopherol | | | | recovery |
|---|---|---|---|---|---|
| (origin) | A | B | Υ | σ | rate |
| Soy | | | | | |
| starting material | <0.1 | <0.1 | 0.81 | 0.58 | n.b. |
| 3a.TFE | 0.87 | 0.24 | 4.50 | 3.20 | 0.98 |
| 3b.TFE | 0.87 | 0.25 | 4.30 | 3.00 | 0.95 |

Example 4 and Comparative Example 5: Microwave Assisted Reaction of a Soy-Based DDO at Different Temperatures The reaction conditions of example 4 and of comparative example 5, soy MW1 and soy MW2, were similar to those of example 1 except that in example 4 with a power of 0.75 kW and in comparative example 5 with a power of 0.85 kW was heated. The respective mixtures in both trials (soy MW1 and soy MW2) were pumped at a speed of 6 l/h and were heated in example 4 with a power of 0.75 kW and in comparative example 5 with a power of 0.85 kW. By this the product to be heated was at a static working pressure of 25 bar and was heated to a temperature of 170° C. (example 4) or 195° C. (comparative example 5).

The temperature of 170° C. and 195° C. was measured immediately when leaving the irradiation zone using Pt100 temperature sensor.

After removal of all accompanying components the respective resulting organic phase was measured by means of HPLC using respective tocopherol calibration standards. A further concentration by separation of the formed fatty acid methyl ester (FAME) by means of distillation has been omitted in both cases.

TABLE 5 tocopherol contents in a soy-based DDO prior to and after micro wave assisted reaction at 170° C. (example 4) and at 195° C. (comparative example 5)

| DDO (orign) | tocopherol | | | | |
|---|---|---|---|---|---|
| | α | β | γ | σ | sum |
| Soy-DDO | 0.15% | 0.05% | 0.82% | 0.50% | 1.52% |
| example 4 (170° C.) | 0.19% | n.n | 0.77% | 0.51% | 1.47% |
| comparative example 5 (195° C.) | n.n | n.n | 0.15% | <0.1% | 0.15% |

Table 5 shows the measured values compared to the starting mixture (soy). While a recovery rate of 96% on all tocopherols was determined at 170° C. in the first run, this is reduced to 10% for reaction at 195° C. under otherwise same conditions.

The invention claimed is:

1. A continuous process for concentrating or separating of vitamin E, sterols and/or terpenes from oily or fatty mixtures of biological origin comprising:
   a) providing a reaction mixture containing an oily or fatty mixture of biological origin, at least a monohydric alcohol and at least an acidic catalyst,
   b) continuously conducting the reaction mixture through a reactor which has a heating zone in which the reaction mixture is heated to a temperature between 100° C. and 190° C., measured with a temperature sensor immediately after leaving the heating zone, and in which the reaction mixture is under such pressure, that the reaction mixture is in liquid, critical or supercritical state,
   c) adjusting the flow velocity of the reaction mixture that its dwell time in the heating zone is up to 10 minutes,
   d) separating the product mixture from step c) into a polar phase containing the glycerol formed during the transesterification, the non-reacted monohydric alcohol, the acidic catalyst, and the reaction water that has been formed during the esterification of the oily or fatty mixture, and into a non-polar phase containing the fatty acid esters, that have been formed during the esterification and transesterification, and therein dissolved and/or dispersed secondary ingredients, and
   e) separating the fatty acid esters formed by esterification and by transesterification from the non-polar phase from step d) and forming a residue containing vitamin E, sterols and/or terpenes.

2. The process according to claim 1, wherein the oily or fatty mixture is of vegetable origin.

3. The process according to claim 1, wherein the oily or fatty mixture is a DDO, an OPRC or a FAD.

4. The process according to claim 1, wherein the process is utilized for separation or concentration of vitamin E, β-sitosterol, stigmasterol and/or campestol.

5. The process according to claim 1, wherein the monohydric alcohol is an aliphatic monohydric alcohol with one to six carbon atoms or a mixture thereof.

6. The process according to claim 1, wherein the acidic catalyst is an acidic inorganic, metal-organic or organic compound.

7. The process according to claim 1, wherein the reaction mixture in the heating zone is treated with thermal energy for a time period of up to 8 minutes.

8. The process according to claim 1, wherein the reaction mixture experiences a temperature rise in the heating zone and has a temperature between 100° C. and 190° C. when leaving the heating zone.

9. The process according to claim 1, wherein the reaction mixture in the reactor is under a pressure between 2 and 250 bar so that the reaction mixture in the heating zone is in liquid, critical or supercritical state.

10. The process according to claim 1, wherein a lingering line is connected to the heating zone of the reactor and wherein the reaction mixture after the dwell time in the heating zone remains for a retention period of up to 30 minutes.

11. The process according to claim 1, wherein the required heating in the heating zone is effected by heat exchangers or by electromagnetic radiation.

12. The process according to claim 11, wherein the heating zone is in the form of a pressure-resistant, microwave transparent pipe, which is located in a suitably sized cavity resonator which is able to produce a resonant electromagnetic field of appropriate field strength, such that the reaction product is heated by a dielectric heating mechanism.

13. The process according to claim 12, wherein the cavity resonator is operated in a mono mode.

14. The process according to claim 12, wherein the electromagnetic radiation has a frequency in the range from 300 MHz to 30 GHz.

15. The process according to claim 1, wherein the separation of the acid catalyst, of the glycerol formed during the reaction, of the non-reacted monohydric alcohol, of the water formed during the reaction and of the fatty acid esters formed by transesterification from the reaction mixture is effected by phase separation, by membrane separation, by extraction, by distillation or by a combination of these measures.

16. The process according to claim 15, wherein the separation of the acid catalyst, of the glycerol formed during the reaction, of the non-reacted monohydric alcohol, of the water formed during the reaction and of the fatty acid esters formed by transesterification from the reaction mixture is effected by a multi-stage separation process.

17. The process according to claim 16, wherein the glycerol formed by transesterification, the water formed during the reaction, the non-reacted alcohol and the acid catalyst are separated from the reaction mixture in a first stage by phase separation and the fatty acid esters formed by esterification and by transesterification are isolated from the reaction mixture in a second stage, whereby in the sump a mixture comprising vitamin E, sterols and/or terpenes remains.

18. The process according to claim 1, wherein the residue comprising vitamin E, sterols and/or terpenes from step e) is further worked-up to isolate the desired ingredients by distillation, by recification, by stripping, by freezing, by fractionated crystallization, by sublimation, by freeze drying, by chromatographic processes, or by extractive processes.

19. A method of recovering vitamin E, sterols or terpenes from oily or fatty mixtures of biological origin comprising utilizing heat exchangers or a microwave applicator.

20. The process according to claim 2, wherein the oily or fatty mixture is of vegetable origin and is selected from acai oil, algae oil, apricot kernel oil, argan oil, avocado oil, babacu oil, cotton seed oil, ben oil, borage oil, nettle seed oil, cashew shell oil, cupuaçu butter, thistle oil, peanut oil, safflower oil, hemp oil, rosehip seed oil, hazelnut oil, jathropha oil, jojoba oil, coffee bean oil, cocoa butter, camellia oil, coconut oil, cumin oil, pumpkin seed oil, linseed oil, cameline oil, macadamia oil, corn oil, almond oil, mango butter, poppy-seed oil, evening primrose oil, olive oil, palm oil, palm kernel oil, papaya seed oil, pecan oil, perilla oil, pistachio oil, rapeseed oil, rice oil, castor oil, sea buckthorn seed oil, sea buckthorn oil, black cumin oil, mustard oil, sesame oil, shea butter, soybean oil, sunflower oil, grape seed oil, tung oil, walnut oil, watermelon seed oil or wheat germ oil.

* * * * *